United States Patent [19]

Shampanier

[11] 4,184,776
[45] Jan. 22, 1980

[54] MIXING AND DISPENSING OF DENTAL AND LIKE MATERIALS

[76] Inventor: Abraham Shampanier, 8 Tel-Hay St., Haifa 33142, Israel

[21] Appl. No.: 940,316

[22] Filed: Sep. 7, 1978

[51] Int. Cl.² ............................................. B01F 7/20
[52] U.S. Cl. .................................. 366/198; 220/4 E; 366/199; 366/602
[58] Field of Search .............. 366/198, 199, 204, 206, 366/207, 602, 605, 233, 235, 239, 240, 247, 261, 297, 279, 189, 325, 326; 220/4 E, 4 B, 23.4

[56] References Cited

U.S. PATENT DOCUMENTS

| | | | |
|---|---|---|---|
| 2,603,461 | 7/1952 | Marienthal | 366/605 |
| 2,939,248 | 6/1960 | Beck | 220/4 E |
| 2,965,363 | 12/1960 | Worden | 366/605 |
| 3,054,600 | 9/1962 | Marsh | 366/297 |
| 3,092,277 | 6/1963 | Brim | 220/4 E |
| 3,521,785 | 7/1970 | Bergmann | 220/23.4 |
| 3,814,387 | 6/1974 | Ahrens | 366/602 |

Primary Examiner—Robert W. Jenkins
Attorney, Agent, or Firm—LeBlanc, Nolan, Shur & Nies

[57] ABSTRACT

A support casing mounts a laterally extending guide track system for positioning an open top receptacle in mixing position where it receives an overhanging bladed rotor carried by a gear box connected to a drive motor. The receptacle is longitudinally split with a guide flange around its open upper end and when mounted on the track system its lower end is tightly pocketed in a flanged fitting, the flanges of the receptacle and fitting sliding into upper and lower tracks of the guide track system. After mixing the receptacle may be removed from the track system and a plunger inserted for controlled dispensing of the mixed material through an opening in the receptacle bottom.

9 Claims, 6 Drawing Figures

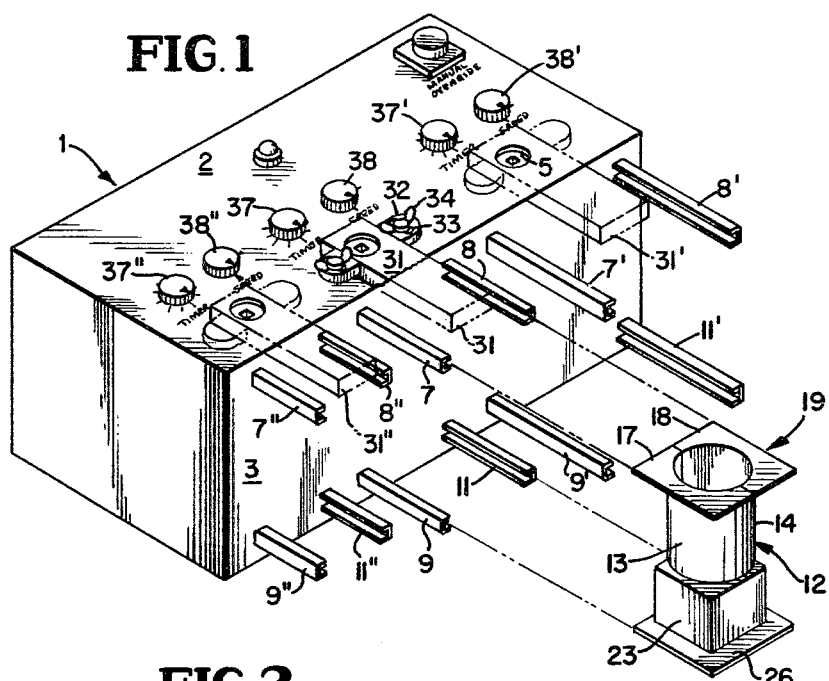
FIG. 1
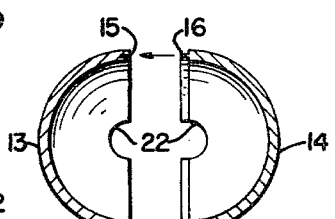
FIG. 3
FIG. 4
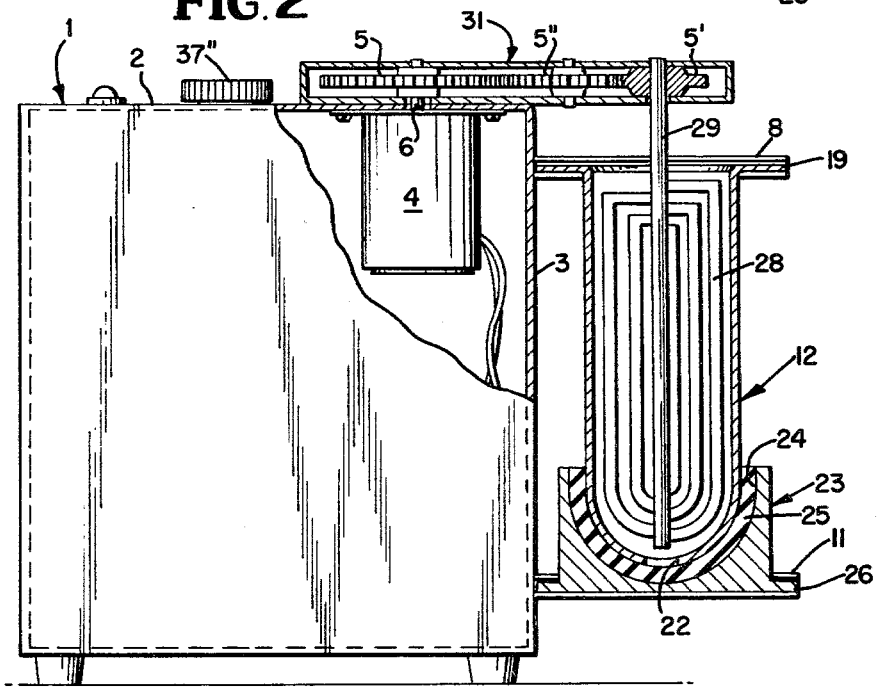
FIG. 2
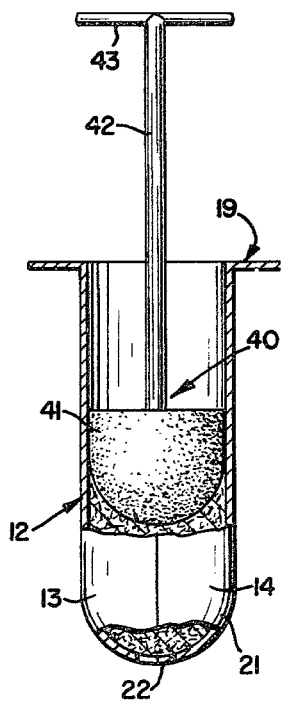
FIG. 5
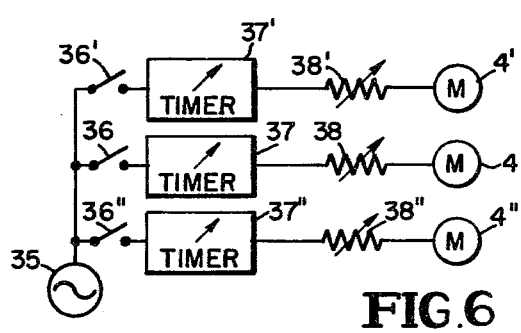
FIG. 6

MIXING AND DISPENSING OF DENTAL AND LIKE MATERIALS

This invention relates to the mixing and metered controlled dispensing of dental and like material and is of particular merit where the material should be dispensed immediately following mixing.

For example materials utilized in the practice of dentistry, such as ingredients of impression alloys and ingredients of cementing mixtures and others must be mixed near the time of actual use. These include powders, liquids, pastes and various combinations of the same. The materials include silicon impression materials, polysulfide materials, polyethers, zinc oxide combinations, bite registration materials, plasters, plastics such as acrylics, tissue conditioning materials, cements, and many others.

Mixing devices for dental material have been known and many provide controls for regulating mixing. In known devices the materials may be mixed in a receptacle from which the mixed material is later extracted for use, or in many instances the materials are mixed on a platform surface which may be cooled or heated to regulate temperature and the dentist removes quantities as they are to be used from the surface as by a syringe.

The present invention provides an arrangement wherein the materials may be thoroughly mixed in one or more receptacles mounted on a mixing device, and each receptacle may be removed from the device ready for immediate controlled dispensing of the mixed material in needed quantities.

It is therefore the major object of the present invention to provide for the ready mixing and metered controlled dispensing of these materials involving a receptacle that may serve both in mixing and dispensing and which is easily used and cleaned.

A further object of the invention is to provide a novel arrangement for mixing materials such as those used in the practice of dentistry where a receptacle may be mounted for mixing on a mixing device and then removed ready for dispensing the mixed materials.

Pursuant to the foregoing object the invention contemplates as other objects a novel mixing device wherein one or more receptacles may be selectively mounted in association with motor driven rotors and equipped with timers and motor speed controls. The invention also advantageously provides a novel receptacle structure that has a upper and lower flange structure for slide guide mounting on a track system of the mixing device, has a metered opening in its bottom for dispensing, and is readily separable into easily cleaned components.

These and other novel objects and features of invention will become apparent as the description proceeds in connection with the associated drawings.

BRIEF DESCRIPTION OF DRAWINGS

FIG. 1 is a generally perspective view showing a mixing assembly;

FIG. 2 is a side elevation partially broken away and in section showing the receptacle in its mixing environment;

FIG. 3 is a generally perspective view showing the separated receptacle halves;

FIG. 4 is a transverse section showing the interfitting relationship of the receptacle halves;

FIG. 5 is a partly schematic, partly sectioned view showing the dispensing phase of the invention; and FIG. 6 is a schematic electrical and control circuit diagram.

PREFERRED EMBODIMENTS

Referring to FIGS. 1 and 2 the mixing apparatus comprises a housing 1 having a top wall 2 and a front wall 3. An electric motor 4 is secured upon the bottom of wall 2 which is recessed to expose the upper end of motor output shaft 6.

A pair of upper opposed U-shaped slide guide track members 7 and 8 are fixedly secured at the same level to front wall 3 and project outwardly away from wall 3. Track members 7 and 8 have their open sides facing each other. A similar pair of fixed lower slide guide track members 9 and 11 project away from wall 3 at the same level below track members 7 and 8. Track members 7 and 8 are disposed in a common horizontal plane, and track members 9 and 11 are disposed in a common horizontal plane. Track members 7 and 9 are disposed in a common vertical plane, as are track members 8 and 11. Thus track members 7, 8, 9 and 11 cooperate to define a fixed slide guide track system on which may be mounted a mixing/dispensing receptacle as will appear.

The hollow-tubular mixing/dispensing receptacle 12 consists essentially of two matching parts 13 and 14. As shown in FIGS. 3 and 4, each part 13 and 14 is generally semi-cylindrical and they are formed along their opposed longitudinal edges with mating female and male formations 15 and 16 capable of joining, when the parts are pushed together for the mixing operation of FIG. 2, with a tight frictional fit, so that together they define an open top tubular body.

The upper ends of parts 13 and 14 are formed with flat flange portions 17 and 18 that define a rectangular receptacle mounting flange 19 surrounding the upper open end of the receptacle body when the parts are pushed together. The dimensions of flange 19 are such as to slidingly fit into the upper guide tracks 7, 8.

The lower ends of parts 13 and 14 taper preferably in a rounded manner so that when the parts are pushed together they form at the lower end of the receptacle an effective dispensing nozzle arrangement of reducing taper, and the lower edge of each part 13 and 14 is formed with a semi-circular edge recess, so that in the assembly a small diameter receptacle discharge opening 22 is provided.

During the mixing phase of the invention the receptacle 12 is mounted on the fixed slide guide track system as shown in FIG. 2. The upper flange 19 slides smoothly in the horizontal guide track provided by members 7 and 8.

The lower end of receptacle 12 is enclosed in a fitting 23 that has an upper generally semi-spherical open pocket 24 lined with a resilient material 25 such as rubber. Pocket 24 is so dimensioned as to fit snugly upon the lower tapered end of the receptacle body, with the rubber lining under compression, so that opening 22 is sealed closed and the rubber in effect exerts a non-slip gripping action which tends to hold the assembled parts 13 and 14 together and against rotation during a vigorous mixing operation.

The lower end of fitting 23 is a flat rectangular flange 26 of the same external dimensions as receptacle flange 19 and it slides smoothly into lower guide track members 9 and 11. The vertical spacing between the upper and lower guide track pairs is such that when the receptacle with its fitting 23 thereon is mounted in the guide track system an effective longitudinal compression force is exerted tending to tightly retain the receptacle in the guide track system, as well as maintain the receptacle parts together.

Mixing of the material in the receptacle is accomplished by a bladed rotor 28 carried by a vertical shaft 29 extending down from an overhanging gear box 31 mounted on housing 1. Gear box 31 is removably and adjustably mounted on the upper side of the top wall 2 by means of wings 32 having slots 33 through which extend wing screws 34 threaded into wall 2.

Gear box 31 contains a meshed reduction gear train for connecting the motor shaft 6 to the rotor shaft 29, and comprises a first gear 5 socketed or otherwise adapted for coupling with the motor shaft 6 when gear box 31 is mounted on housing 1, an output gear 5' fixed to the upper end of shaft 29 and one or more intermediate gears 5".

Thus in practice the bladed rotor 28 is mounted on the gear box so that, after the receptacle 12 containing material to be mixed has been mounted in the fixed guide system, the gear box may be located and lowered to thrust the rotor into the open upper end of the receptacle and in substantially the same motion couple gear 5 in drive relation to the motor shaft 6 when the gear box seats in wall 2. Then screws 34 are tightened, after any necessary swivel adjustment of the gear box should shaft 29 be not exactly concentric with the receptacle.

With the receptacle in mixing position and the gear box 31 installed, motor 4 may be actuated to rotate bladed rotor 28 for the mixing period.

As shown in FIG. 6, motor 4 is in an electrical circuit wherein power from a source 35 may be connected through a manual control switch 36, an adjustable timer switch 37, and an adjustable motor speed control resistance 38.

At opposite sides of the track system 7, 8, 9 and 11 may be mounted substantially identical track systems 7', 8', 9' and 11' and 7", 8", 9" and 11" for mounting other receptacles of the type of FIG. 3 containing other or different materials so that several receptacles can mix material at the same time. Each of these added receptacles will accept a bladed rotor (not shown) depending from a gear box 31' and 31" and driven by a motor 4' and 4". As shown in FIG. 6, the motors 4' and 4" have switches 36', 36" timers 37', 37" and speed control resistors 38', 38" for controlled individual mixing operations. Differences in humidity and temperature from time to time in dental laboratories can render the reproducible mixing of many materials difficult. By reason of the foregoing timing and mixing speed controls reliable and reproducible mixing is obtainable.

For carrying out the mixing operation the motor timer and speed controls are set prior to closing the manual switch in each circuit. When the mixing operation is complete for any receptacle it is removed from its track system, the associated gear box being moved away to remove the rotor, and is now ready for dispensing the mixed material.

FIG. 5 shows the dispensing operation whereby after removal of fitting 23 the mixed material may be immediately dispensed from the receptacle. In dispensing a plunger-like feed device 40 having a smooth surfaced head 41 sized to slidably and rotatably fit to the open upper end of the receptacle and exert pressure on the upper end of the column of mixed material is used.

Device 40 has an operating stem 42 longer than the length of the receptacle, for full dispensing, and has a handle 43 for facilitating movement of the device.

The longitudinal friction fit between the receptacle halves is strong enough to keep them together during the dispensing operation, particularly when properly held in the operator's hands, and it permits them to be readily separated for thorough cleaning after all material is dispensed.

The invention has many advantageous features.

The several individual guide track systems and motor driven rotors enable several different and independent mixing operations to take place at the same time. The use of the same receptacle for both mixing and dispensing makes the operations more efficient. The split receptacle structure facilitates cleaning. The novel plunger controlled dispensing avoids waste of expensive materials. The cylindrical body of the receptacle 12 may be transparent with a longitudinal scale associated with the plunger and the size quantity dispensing.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. Apparatus for mixing materials such as dental materials comprising a support having fixed laterally extending guide track means, an open top receptacle adapted to be removably mounted in mixing position on said guide track means, motor means on said support, and a mixing rotor assembly comprising a gear box removably mounted on said support and having means for mounting a depending bladed rotor adapted to extend through the open mouth of said receptacle and a detachable reduction gear connection to said motor.

2. The apparatus defined in claim 1, wherein said gear box is mounted on said support in overhanging relation to said guide track system and houses gearing extending from a coupling to said motor to a shaft mounting the bladed rotor.

3. The apparatus defined in claim 1, wherein said motor is an electric motor and motor circuit means is carried by said support and includes a manual switch, an adjustable timer switch and a variable speed control for said motor.

4. A mixing and dispensing receptacle comprising a generally cylindrical body having an open upper end for receiving a plunger and surrounded by a mounting flange, and a tapered lower end that is closed except for a central dispensing opening of predetermined size, said receptacle being longitudinally split into sections that may be readily separated for thorough cleaning and the like.

5. The mixing receptacle defined in claim 4, wherein the longitudinal edges of said sections have mated frictional holding means.

6. Apparatus for mixing materials such as dental materials comprising a support having fixed laterally extending guide track means, an open top receptacle adapted to be removably mounted in mixing position on said guide track means, motor means on said support, a mixing rotor assembly mounted on said support having a bladed rotor adapted to extend through the open mouth of said receptacle and a reduction gear connection to said motor, said mixing rotor assembly comprising a gear box that is mounted on said support in overhanging relation to said guide track system and housing gearing extending from a coupling to said motor to a depending shaft mounting the bladed rotor, and means for removably and adjustably mounting said gear box on said support, said coupling being of the type as to be detachable when the gear box is removed from the support.

7. Apparatus for mixing materials such as dental materials comprising a support having fixed laterally extending guide track means, an open top receptacle adapted to be removably mounted in mixing position on said guide track means, motor means on said support, and a mixing rotor assembly mounted on said support having a bladed rotor adapted to extend through the open mouth of said receptacle and a reduction gear connection to said motor, said track means comprising upper and lower tracks, said receptacle being flanged at its upper end and seated in a flanged fitting at its lower end, and the flanges of said receptacle and fitting sliding into said upper and lower tracks respectively for mounting the receptacle on said guide track assembly.

8. The apparatus defined in claim 7, wherein said receptacle comprises a longitudinally split section structure having a bottom opening of reduced size with the sections frictionally held together in assembly, and said fitting forming a tight holding pocket enclosing and closing the bottom of said receptacle.

9. Apparatus for mixing materials such as dental materials comprising a support having fixed laterally extending guide track means, an open top receptacle adapted to be removably mounted in mixing position on said guide track means, motor means on said support, and a mixing rotor assembly mounted on said support having a bladed rotor adapted to extend through the open mouth of said receptacle and a reduction gear connection to said motor, there being several individual guide track systems projecting laterally from said support, each associated with an individual motor and mixing rotor assembly whereby several individual mixing operations can be carried out at the same time.

* * * * *